United States Patent
Moskal

(10) Patent No.: US 8,969,817 B2
(45) Date of Patent: Mar. 3, 2015

(54) MATRIX DEVICE AND METHOD FOR DETERMINING THE LOCATION AND TIME OF REACTION OF THE GAMMA QUANTA AND THE USE OF THE DEVICE TO DETERMINE THE LOCATION AND TIME OF REACTION OF THE GAMMA QUANTA IN POSITRON EMISSION TOMOGRAPHY

(75) Inventor: Pawel Moskal, Rybna (PL)

(73) Assignee: Uniwersytet Jagiellonski, Krakow (PL)

(*) Notice: Subject to any disclaimer, the term of this patent is extended or adjusted under 35 U.S.C. 154(b) by 477 days.

(21) Appl. No.: 13/383,581

(22) PCT Filed: Jul. 15, 2010

(86) PCT No.: PCT/PL2010/000061
§ 371 (c)(1),
(2), (4) Date: Mar. 25, 2012

(87) PCT Pub. No.: WO2011/008118
PCT Pub. Date: Jan. 20, 2011

(65) Prior Publication Data
US 2012/0175523 A1    Jul. 12, 2012

(30) Foreign Application Priority Data
Jul. 16, 2009 (PL) .......................... 388556

(51) Int. Cl.
*G01T 1/164* (2006.01)
*G01T 1/29* (2006.01)

(52) U.S. Cl.
CPC .................... *G01T 1/2985* (2013.01)
USPC .................................. 250/363.03

(58) Field of Classification Search
USPC ...................................... 250/363.03
See application file for complete search history.

(56) References Cited

U.S. PATENT DOCUMENTS

| 3,978,337 | A | 8/1976 | Nickles |
| 4,454,424 | A | 6/1984 | Strauss |
| 7,968,850 | B2 * | 6/2011 | Chinn et al. ............ 250/363.03 |
| 8,859,973 | B2 * | 10/2014 | Moskal ................... 250/363.01 |
| 2008/0111081 | A1 * | 5/2008 | Chuang ................... 250/363.03 |
| 2009/0324042 | A1 * | 12/2009 | Laurence et al. ............. 382/131 |

FOREIGN PATENT DOCUMENTS

FR        2925698 A1    6/2009

* cited by examiner

*Primary Examiner* — Christine Sung
(74) *Attorney, Agent, or Firm* — Mark M. Friedman

(57) ABSTRACT

The subject matters of the invention is a matrix device and method for determining the place and time of the gamma quanta interaction as well as the use of the device for determining the place and time of the gamma quanta interaction in positron emission tomography.

7 Claims, 8 Drawing Sheets

MATRIX DEVICE AND METHOD FOR DETERMINING THE LOCATION AND TIME OF REACTION OF THE GAMMA QUANTA AND THE USE OF THE DEVICE TO DETERMINE THE LOCATION AND TIME OF REACTION OF THE GAMMA QUANTA IN POSITRON EMISSION TOMOGRAPHY

The subject matter of the invention arc a matrix device and method for determining the location and time of reaction of the gamma quanta and the use of the device to determine the location and time of reaction of the gamma quanta in positron emission tomography. More specifically the invention describes a solution to determine the spatial distribution of concentration of selected substances in the body and changes of their concentration in time.

Positron emission tomography is based on the determination of the spatial distribution of concentration of selected substances in the body and the changes of this concentration in time. To this end, the patient is administered pharmaceuticals marked with radioactive isotope emitting positrons. Radioactive market is chosen so that it decays with the emission of positrons. The tomography uses the fact that the positron from the marker and electron from an atom of the body annihilate in contact with each other and their mass is converted into energy in the form of gamma quanta. Most frequently these are two gamma quanta flying back to back along the line with an exactly defined energy equal to 511 keV. The annihilation occurs typically only a few millimeters from the decay of the marker. This fact determines a natural limit of sharpness of the PET image. PET tomograph allows to locate the radioactive marker by measuring the direction of flight of the annihilation quanta. Radiation detectors are usually arranged in layers forming a ring around the patient. Currently, all commercial PET tomographs use inorganic scintillator material for detection. The energy of gamma quantum hitting the scintillator can be transferred partially or entirely to an electron of the material, which then produces flash of lights through ionization and deexcitation of atoms or molecules of the scintillator. These flashes are then converted to electrical pulses by photomultipliers connected to the scintillators. The number of photons generated in scintillator material is proportional to the energy that a quantum transferred to the electron. In turn, charge of electrical signal generated by photomultipliers is proportional. to the number of photons incident on the photomultiplier window. For the energy of gamma quanta amounting to 511 keV there are two significant processes called photoelectric effect and Compton effect. In the first process gamma quantum transfers to the electron its entire energy, while in the second process only part of the energy is transferred depending also on the electron scattering angle. As a result of these processes, the spectrum of charge of registered signals consists of a continuous distribution corresponding to Compton effect and a peak corresponding to the photoelectric effect. Separation of this maximum allows to distinguish the cases where the annihilation quanta of energy 511 keV reached scintillator undisturbed from all the others cases. In the current tomographs one use scintillating crystals, made usually in size of about 5 cm×5 cm and which are additionally blazed into smaller pieces with dimensions of 0.5 cm×0.5 cm separated from each other with reflecting material. The end of each scintillating module is connected to photomultipliers which convert light into electrical impulses. This arrangement permits to determine, with the accuracy equal to the size of the small unit, the position where the gamma quantum reacted. Therefore, in the further analysis, one assumes that the quantum was absorbed in the middle of the unit. This causes the smearing of the image, the greater, the farther foam the axis of the tomograph the annihilation occurred, and the larger is the scintillator module. One try to improve the image resolution by calculating the point of annihilation along the line of flight of the quanta by measurement of the time difference between the arrival of the gamma quanta to the detectors. In the literature this technique is known as TOF (time of flight), and tomographs which use the time measurements are termed PET-TOF. For efficient application of this technique one requires the time resolution in order of tens of picoseconds, unattainable in the current tomographs based on inorganic scintillators.

In Patent Application U.S. 2006060823 (published at Mar. 26, 2006) an invention for a radiation detection scintillator using a flexible composite is described. This composite is created by the rapid mixing of dense, doped with rare earth elements oxyorthosilicate (eg, LSO: Ce, LSO: Sm, or GSO: Ce) with a binder which is transparent to the radiation emitted from the scintillator. Composites are uniform and can be made in large sizes and different shapes. Importantly, such a composite can emit radiation in the range of responses corresponding to the photomultiplier (400 nm) which increases the efficiency of the detector.

In Patent Application U.S. 2008237470 (published at Oct. 2, 2008) a scintillation detector containing nanoparticles of scintillation component embedded in a matrix of plastic material is presented. The nanoparticles can be made from materials such as metal oxides, metal oxohalides, oxysulphides metals or metal halides. New ways of producing nanoparticles were developed in which particles can be coated by organic material or polymers before setting into a plastic matrix. The technique of matching the reflectance of the plastic matrix by the use of titanium dioxide nanoparticles was also developed. Scintillator can be joined with at least one photo-detector system forming a scintillation detector, which can be adapted for use in X-ray imaging systems, such as digital X-ray imaging, mammography, CT, PET or SPECT, or in safe detectors of radiation and detectors of the underground radiation.

In patent applications U.S. 2008296505 (published at Dec. 4, 2008) and WO 2007082126 (published at Jul. 19, 2007) the way to reconstruct the image of the time of flight (TOF) is described. It includes obtaining of the outline of the investigated object in the test area (14) of imaging system (10). Events related to the radiation emitted from the object are recorded and converted into electronic data. The electrical signals corresponding to the incident radiation from outside the object are removed, thus the final images are reconstructed from the remaining electronic data.

In Patent Application U.S. 2004173752 (published at Sep. 9, 2004) one has , demonstrated that in case of certain hybrid organic/inorganic perovskite as the scintillator material, radiation is generated in the optical range at a rate of around subnanoseconds, and the same scintillator can be used as a detector of gamma radiation in PET tomography. PET scanner, according to the invention, contains a scintillator-based hybrid organic/inorganic perovakite compounds selected from the compounds of specific formula. Speed of response known for scintillators presently used in PET tomography is very limited, because there is a restriction of resolution obtained by this method. In order to solve this problem, one has estimated that the scintillator response rate should be approximately 0.1 ns. The development of such scintillator allowed to limit temporal resolution obtained with this Method. In the described application methods of manufacture and the composition of such scintillators on the order of several cubic centimeters are given. However, in order to achieve spatial resolution along the lines of response, that would be on the order of the natural uncertainty originating from the positron absorption in the body of the patient, the required time resolution should be better than 50 ps and the economic imaging of the entire human body needs fast scintillators on the order of meters in size.

In the Patent Application EP 2047297 (published at Apr. 21, 2008) PET tomograph (100) based on time of flight measurement is presented. It includes the detector (106), system (120) of data acquisition, system of compliance (122) and reconstructing unit (129). Elements for imaging affect the time resolution of the system (100) so that the positron data, which are collected along different lines of response are characterized by different timing resolutions. These time resolutions are used for determining the position of registered events along the corresponding lines of response.

Despite the above described research focused on solutions for determination of the place and time of the interaction of gamma quanta used in positron emission tomography, there is a continuing need for an effective solution for detection of radiation using a plastic scintillator doped with atoms of high atomic number, which would allow to obtain time resolutions needed for the effective application of TOF techniques, as well as for substantial reductions in the cost of production of PET tomographs due to the relatively easy possibility to produce organic scintillators in any size.

The purpose of this invention is to provide resources that could be used to produce solutions for the determination of the place and time of reacting gamma quanta used in positron emission tomography.

The realization of such a particular purpose, and solution of problems described in the state-of-art techniques associated with measuring of time of flight and with limitations of the obtained time resolution, have been achieved in the present invention.

The invention is a matrix device to determine the location and time of interaction of gamma quantum built out of scintillation chamber, characterized in that the chamber contains a scintillation plates constructed out of plastic scintillator preferentially doped with atoms with an atomic number of at least 50 and in that the surface of the scintillation plates reflect photons incident to the surface from the inside at an angle greater than the so-called boundary angle, and in that the photomultipliers constitute a detector wall registering on each side light pulses emerging from the scintillation chamber, and also in that the resulting light pulses are converted into electrical signals by means of matrix of photomultipliers situated between scintillation plates and casing of the whole device, while photomultipliers are attached to the mounting plate which is attached to the housing which shelter and maintain the entire device, which is attached to the frame, in which scintillation plates are embedded. while the mounting plate for supporting of the photomultipliers has a net of cutted holes, whose size and shape are matched to the size and shape of the casing of photomultipliers, while between the photomultipliers and scintillation plates air layer is left and in the first step of data analysis those events are selected for which signals were registered in at least three side layers and in front and back layer of photomultipliers and then to further processing only those signals are taken, which appeared within a fixed time interval, after which the location of quantum reaction in a plate plane (xy) is determined with three independent methods based on the amplitude of the signals from the front and rear photomultiplier layers, on amplitudes of signals from side photomultiplier layers, on time of photomultiplier signals from the front and back layers while as the final result the average weighted with appropriate measurement uncertainties is taken, whereupon from the distribution of signal amplitudes in the photomultipliers in side panels of the plates the depth of gamma quantum interaction (DOI) and LOR lines are determined, then based on the time of signals from all the photomultipliers the point of annihilation along the LOR line is defined, and delivered set of the reconstructed LOR lines and the location of annihilation points along these lines provides a tomographic picture.

Preferably, when the voltage is distributed to the photomultiplier dynodes by the voltage dividers, which are matched to the type of photomultiplier, and that the voltage divider is supplied via voltage cables by the power supply placed in the housing for the electronics adjacent to the casing of photomultipliers, and signals from the photomultipliers are delivered to electronic circuits using signal cables.

Preferably, the scintillation plates am connected by an optical cement whose refractive index is similar to the refractive index of the material from which the scintillator plates are made, while similar refractive indexes minimize the reflection of photons in the place of connection.

Preferably, the scintillator plates are separated from the interior chamber with a lightproof foil.

Preferably, when the plastic cover is seen from the patient's side.

Preferably, the walls of photomultipliers can be divided into the right (P), left (L), top (G) and bottom (D), and registering the light in front (F) and rear (T) part.

Preferably, when the device is presented in FIGS. 1 to 7.

The next subject of the invention is a method to determine the location and time of interaction of gamma quantum, characterized in that the surface of the scintillator plate reflects photons incident to the surface from the inside at an angle greater than the so-called boundary angle, and in that the photomultipliers constitute a detector wall registering on each side light pulses emerging from the scintillator plates, and also in that the resulting light pulses are converted into electrical signals by means of matrix of photomultipliers situated between scintillation plates and casing of the whole device, while photons of light, resulting from absorption of the gamma quantum in the scintillator material that reach the surface of the plate at an angle smaller then the boundary angle fly out and are registered by the photomultipliers surrounding the scintillation chamber, and in the first step of data analysis those events are selected for which signals were registered in at least three side layers and in front (F) and back (T) layer of photomultipliers and then for further processing only those signals are taken, which appeared within a fixed time interval, after which the location of quantum reaction in a plate plane is determined, whereupon based on the distribution of amplitudes of the signals in side photomultipliers the depth of gamma quantum interaction (DOI) and LOR lines ate determined, where on the basis of the point of annihilation and knowledge about amplitudes and times of signals registered by photomultipliers one determines the energy deposited in the scintillation material by gamma quantum and the time of reaction, one calculates the location of annihilation along the LOR line, one determines the point of annihilation, whereupon the delivered set of reconstructed LOR lines and the location of annihilation points along these lines provides a tomographic picture.

Preferably, when a layer of air is left between the photomultipliers and scintillation chamber, and that light signals are registered by a larger number of photomultipliers due to refraction of the line of light coming out of the scintillation plate into the air.

Preferably, when the electronic circuit converts the amplitude and time of emergence of signals to digits, which are sent to the computer in binary form, where on its basis the distribution of density of radioactive marker in the patient's body is reconstructed.

Preferably, when the location of quantum reaction in a plate plane (x-y) is determined with three independent methods based on the position of the photomultipliers and on amplitudes of the signals from the front (F) and rear (R) photomultiplier layers, on amplitudes of signals from side photomultiplier layers, on time of photomultiplier signals from the front and back layers while as the final result the average weighted with appropriate measurement uncertainties is taken.

Preferably, when one determines the depth of gamma quantum interaction (DOI) from the distribution of signal amplitudes in the photomultipliers in side panels of the plates, where on the basis of the point of reaction and knowledge about amplitudes and times of signals registered by photomultipliers one determines the energy deposited in the scintillation material by gamma quantum and the time of reaction, one calculates the location of annihilation along the LOR line, whereupon the delivered set of reconstructed LOR lines and the location of annihilation points along these lines provides a tomographic picture. Preferably, when the energy deposited by gamma quantum in scintillator material and the reaction time is determined taking into account the total number of photomultipliers, which gave a signal due to the reaction of the gamma quantum, the distance between the point of the reaction and the middle of photomultiplier window ($\Delta_{ri}$), the calibration constant ($v_s$) corresponding to the speed of the light signal in the scintillator, and the calibration constant ($\lambda$) indicating attenuation of signal, uncertainty of determination of the amplitude ($\sigma$).

Preferably, when it is used in Positron Emission Tomography.

The next subject of the invention is application of the device as described above in positron emission tomography.

The attached figure provides a better explanation of the substance of a solution, whereby:

Figure 4:
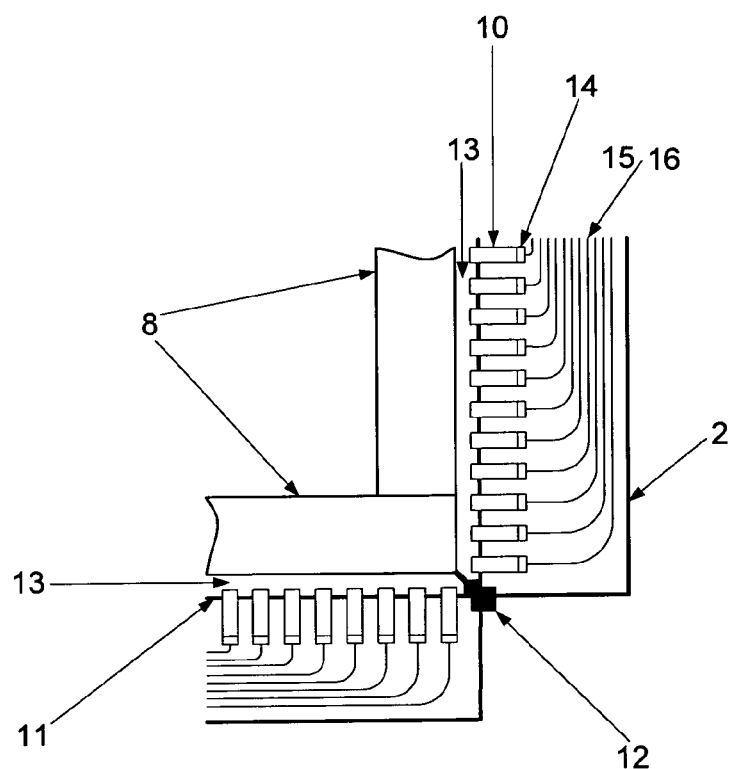
Figure 4A:
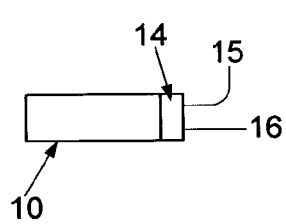
Figure 4B:
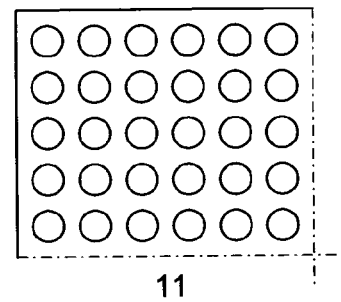
Figure 5:
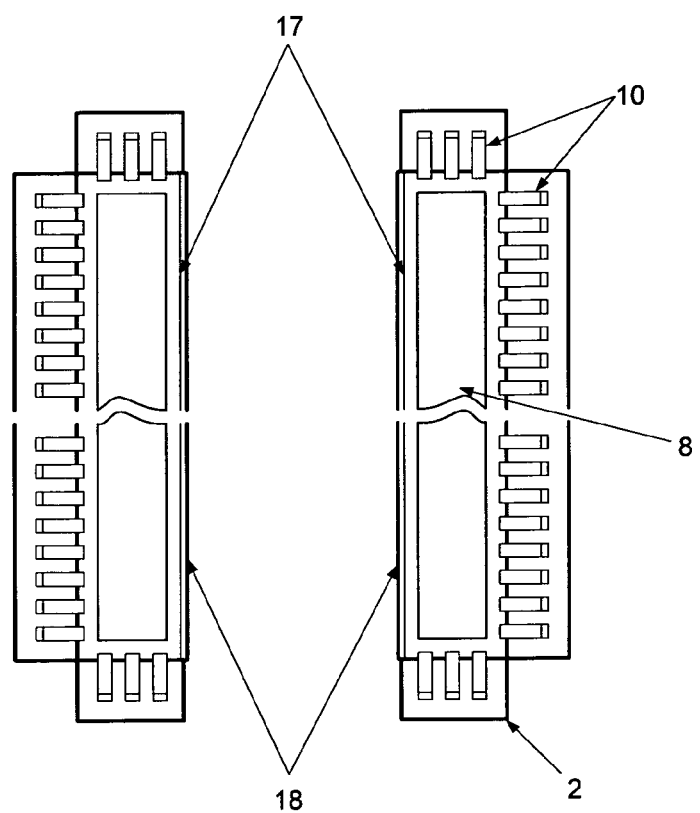
Figure 6:
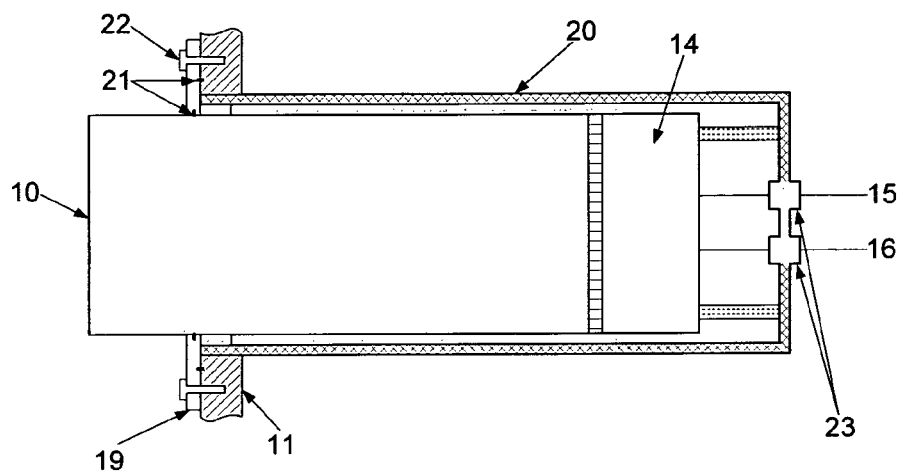
Figure 7:
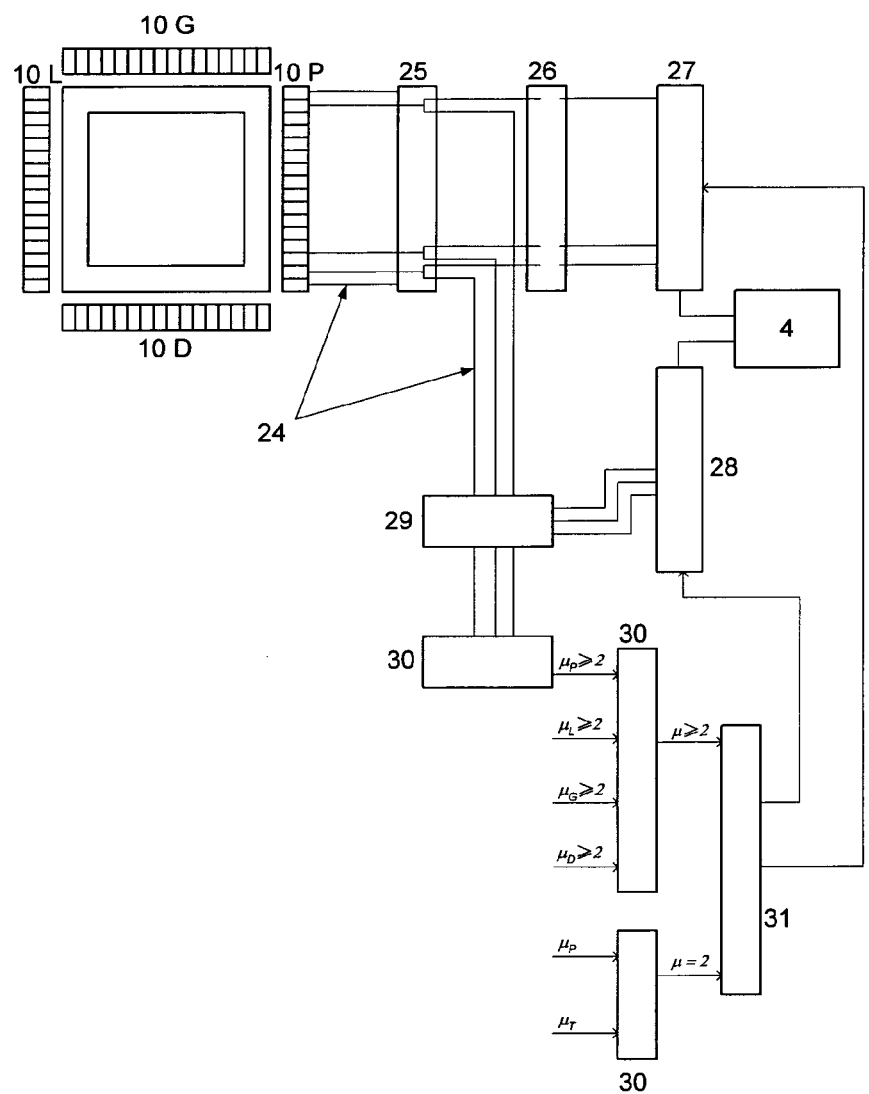
Figure 8:
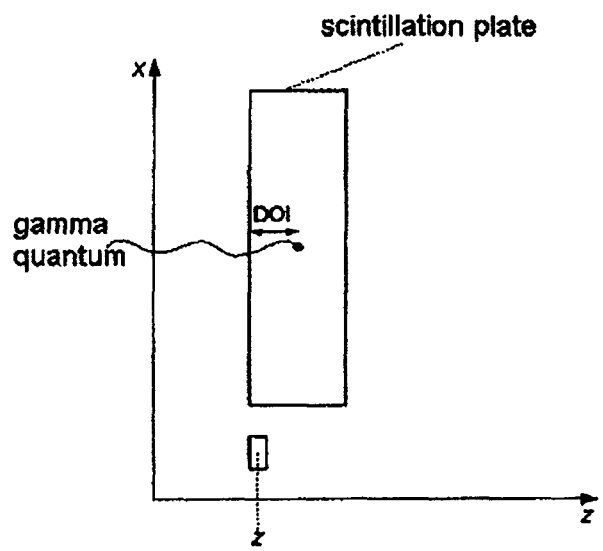
Figure 9:
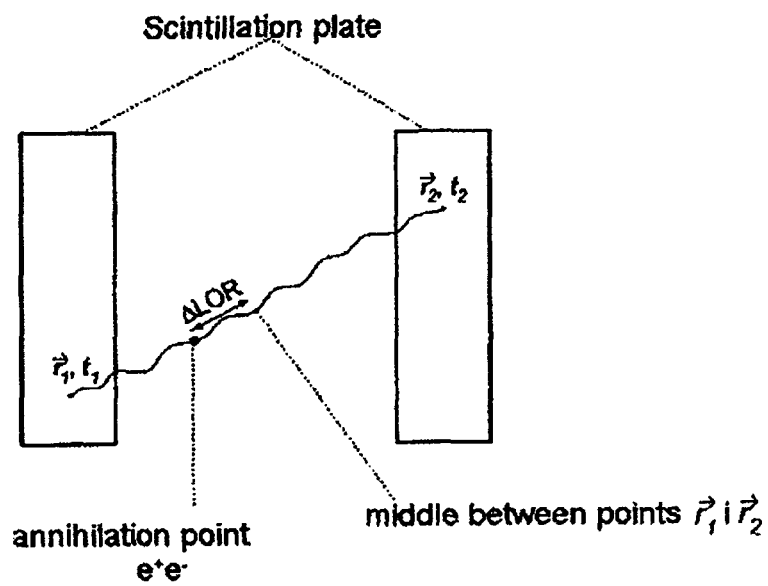

FIG. 4 shows a sample photomultiplier mounting, while FIG. 4a presents a set of photomultiplier and voltage divider, and FIG. 4b a part of the plate 11 for mounting the photomultiplier, FIG. 5 shows a horizontal section of the scintillation chamber with casing 2 and photomultiplier 10;

FIG. 6 shows exemplary light-proof photomultiplier attachment to mounting plate with the handle connected to the photomultiplier tube;

FIG. 7 shows an exemplary logic diagram of the electronic system, which allows to obtain the information about amplitude and time of the impulses generated by photomultipliers;

FIG. 8 shows a gamma quantum and a scintillation plate; FIG. 9 shows an annihilation point between scintillation plates.

Where various markings on the figures indicate:

1—Scintillation chamber for the examination of the patient, 2—housing of the chamber and photomultipliers, 3—housing for electronic circuits, 4—computer for the reconstruction of the tomographic image, 5—monitor, 6—printer, 7—a platform that allows the patient to move into the scintillation chamber, 8—scintillation plates, 9—plates are connected by an optical cement whose refractive index is similar to the refractive index of the scintillator n≈1.58, 10—photomultiplier, while 10 D, 10 G, 101', 10 L, 10 F, 10 T-are the lower, upper, right, left, front and rear wall of photomultipliers, 11—plate for mounting photomultipliers, 12—frame for fixing the scintillation chamber, 13—layer of air, 14—voltage divider, 15, 16—high voltage cables and signal cables; where 15—power cable, 16—signal cable, 17—light-proof foil, 18—plastic shield of the inside of the scintillation chamber, 19—bracket, 20—photomultiplier shield, 21—seal, 22—bolt, 23—light-proof exit of power and signal cables, 24—signal cables, 25—system for signals separation, 26—time-delay system, 27—ADC—charge-to-digit converter, 28—TDC—time-to-digit converter, 29—multichannel discriminator, 30—system to count the multiplicity of signals, 31—coincidence system.

For a better understanding of the solutions below an exemplary embodiment of the invention is presented.

Example

Figure 1:
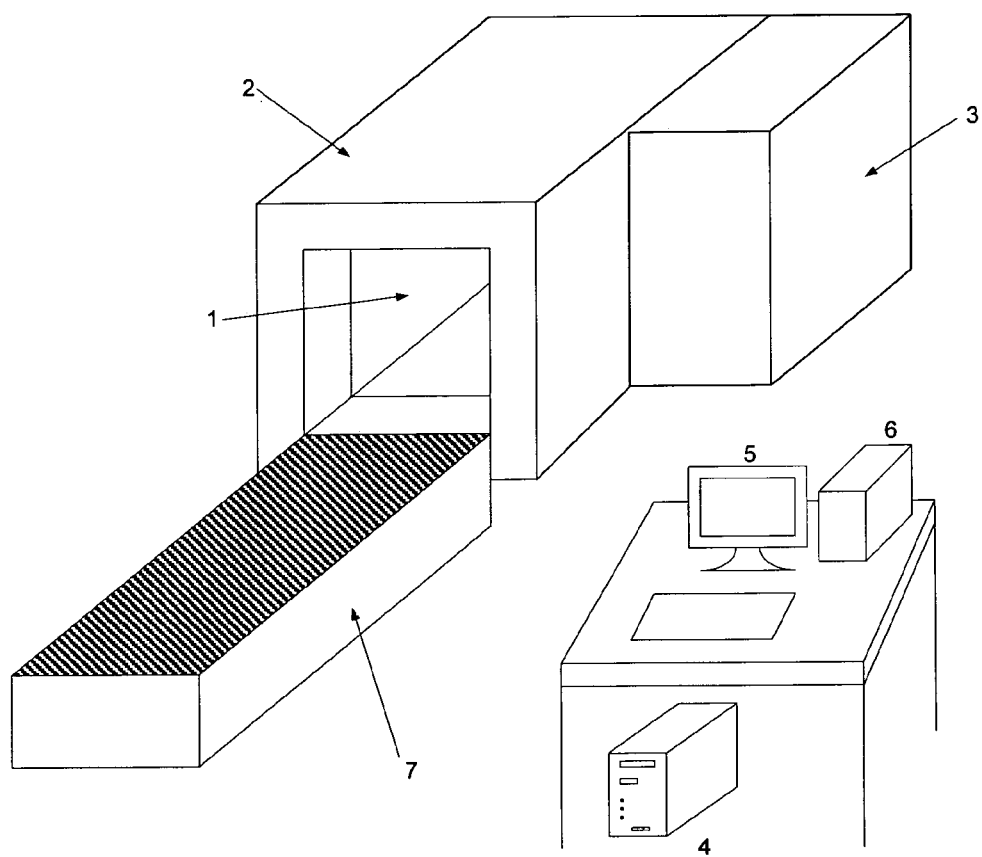
FIG. 1 shows a general scheme of the device, which consists of a scintillation chamber, into which the patient, after inserting the radio-pharmaceuticals, is placed 7.

FIG. 1 shows a general scheme of the device, which consists of a scintillation chamber (1), into which the patient, after inserting the radio-pharmaceuticals, is placed. Gamma-quanta resulting from the decay of radioactive marker in the patient's body produce light flashes in the scintillation chamber. The resulting light pulses are converted into electrical signals by means of matrix of photomultipliers located between the scintillation chamber and casing of the entire unit (2). The signals from the photomultipliers are sent using cables to the electronics located in the housing (3) sticking to the scintillation chamber casing. The electronic circuit converts the amplitude and time of emergence of signals to the digits, which are sent to the computer in binary form (4), where on its basis the distribution of density of radioactive marker in the patient's body is reconstructed. This image can be viewed on the screen (5), printed (6), or saved to disk in the computer. In order to perform the examination the patient is placed on the platform (7), which can be slipped into the scintillation chamber (1) lined from the patient's side with plastic cover (18).

Figure 2:
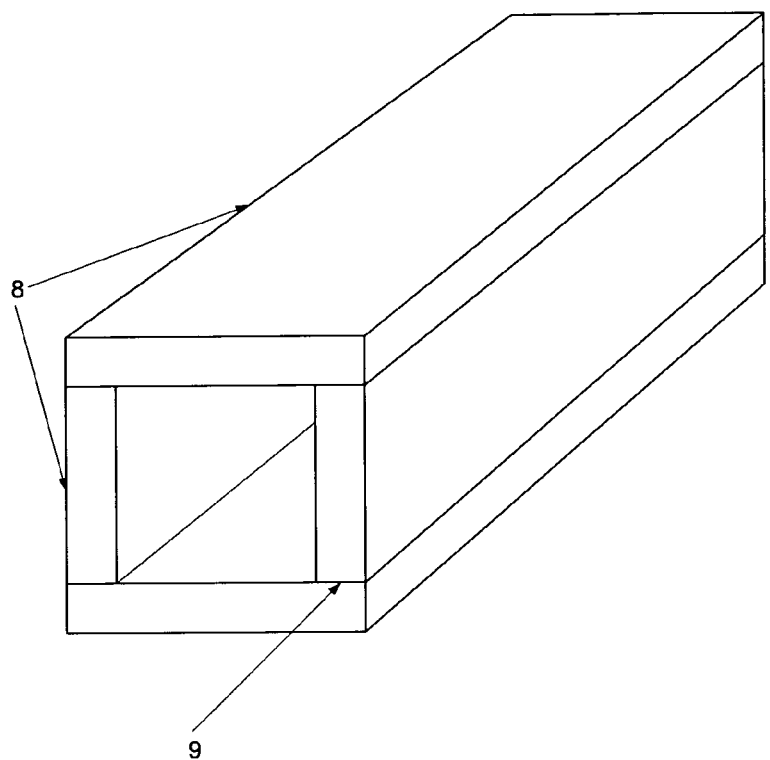
FIG. 2 shows a sample arrangement of scintillation plate 8.

Scintillation chamber (1) consists of strips of plastic scintillator doped with atoms of high atomic number, in this case lead. FIG. 2 shows an exemplary arrangement of scintillation plates (8). Surfaces of the scintillation strips should be cutted with diamond blade, or polished in order to reflect photons incident to the surface from the inside at an angle greater than the so-called boundary angle. Plates are connected by an optical cement (9) whose refractive index is similar to the refractive index of the material from which the scintillation plates are made. Similar coefficients of light minimize the reflection of photons in the place of connection. Photons of light, resulting from absorption of the gamma quantum in the scintillator material that reach the surface of the plate at an angle smaller then the boundary angle fly out and are registered by the photomultipliers surrounding the scintillation chamber.

Figure 3:
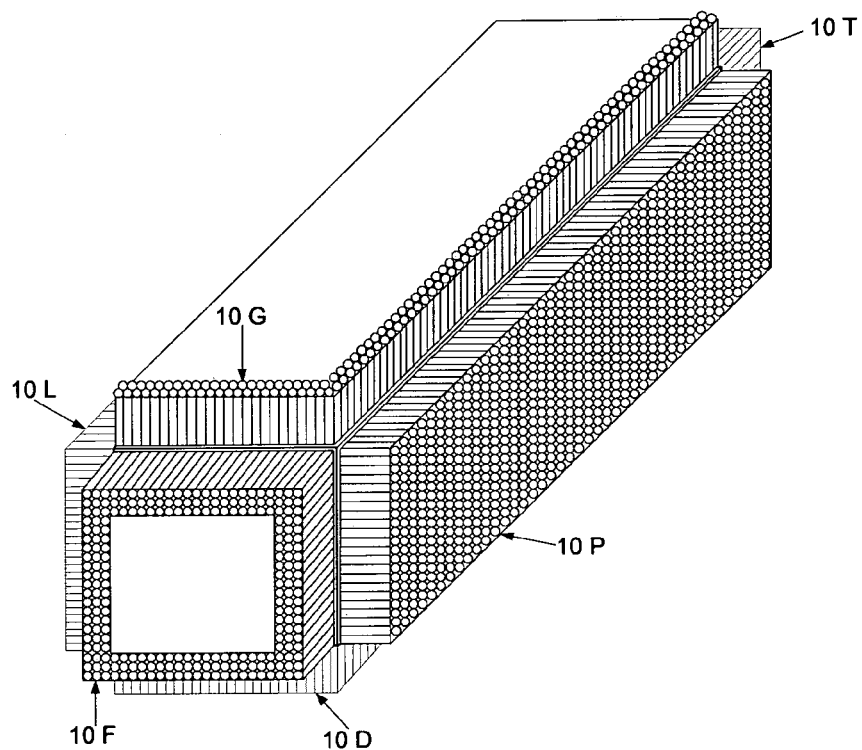
FIG. 3 shows the photomultipliers 10, which form the detection walls registering on each side the light pulses emerging out of the scintillation chamber.

As illustrated in FIG. 3, the photomultipliers 10 constitute detection walls registering from each side light pulses going out from the scintillation chamber. Walls of photomultipliers could be divided into: the side right (10 P), and left (10 L), upper (10 G) and lower (10 D), and recording the light in front (10 F) and rear (10 T).

In FIG. 4 the lower-right corner of the device is shown as an example of photomultipliers mounting.

Photomultipliers are attached to the mounting plate 11, which is attached to the housing which shelter and maintain the entire device 2. To this housing also a frame 12 is attached, in which scintillator plate are embedded 8. The mounting plate for supporting of the photomultipliers has a net of cutted holes, whose size and shape are matched to the size of photomultipliers and the shape of the casing, and the relative arrangement and distance can be optimize in view of the required resolution and cost of the device. Between the photomultipliers and scintillation plates air layer is left 13. It causes, due to refraction of the line of light coming out of the scintillation plate into the air, that light signals are registered by a larger number of photomultipliers, which consequently contributes to the improvement of spatial resolution of the device. Voltage to the photomultiplier dynodes 10 is distributed by the voltage dividers 14, which are matched to the type of photomultiplier. The voltage divider 14 is supplied via voltage cables 15 by the power supply placed in the housing for the electronics adjacent to the casing of photomultipliers, labeled as 3 in FIG. 1. Signals from the photomultipliers are delivered to electronic circuits using signal cables 16.

Scintillation chamber must be optically isolated from the room in which the tomograph operates. Therefore, both the photomultipliers mounting and mounting of the plastic inner of the chamber have to be light-proof. Exemplary schematic solutions are shown in FIGS. 5 and 6.

FIG. 5 shows horizontal section through the scintillation chamber with housing 2 and photomultipliers 10. Scintillation plates 8 are separated from the interior of the chamber with light-proof foil 17. The plastic cover 18 can be seen from the patient's side.

FIG. 6 presents an exemplary light-proof photomultiplier mounting 10 to the plate 11 made by means of handle 19 connected to the shield of photomultiplier 20. Light-proofing is provided by seals 21.

FIG. 7 shows an exemplary logic diagram of the electronic system that allows to obtain information about the amplitude and time of impulses generated by photomultipliers. These in turn are closely connected with time and amplitude of light signals reaching the photomultipliers.

Software to analyze the data in the first step selects those events, for which signals were registered in at least three side layers and in front and back layer of photomultipliers. For further processing only those signals are taken, which appeared within a fixed time interval (several nanoseconds). Then the location of quantum reaction in a plate plane (xy) is determined with three independent methods according to formulas I, II and III, where $$x = \alpha \cdot \frac{\sum_{i=1}^{N_F} A_F^i - \beta}{\sum_{i=1}^{N_F} A_F^i + \sum_{i=1}^{N_T} A_T^i - \gamma}, \quad \text{(Formula I)}$$

where $N_F$ and $N_T$—the number of photomultipliers, which gave a signal in the front (F) and rear (T) layer, $\alpha, \beta, \gamma$—calibration constants $A_F^i$—amplitude of signal of the ith photomultiplier in the front layer, $A_{T1}$—amplitude of signal of the ith photomultiplier in the back layer;

$$x = \frac{\sum_{i=1}^{N_P} x_i A_P^i}{\sum_{i=1}^{N_P} A_P^i}, \quad \text{(formula II)}$$

where $x_i$—x coordinate of the position of ith photomultiplier in a plane P;

$$x = \left( \frac{1}{N_F} \sum_{i=1}^{N_F} t_i^F - \frac{1}{N_T} \sum_{i=1}^{N_T} t_i^T \right) \cdot v + \Delta, \quad \text{(formula III)}$$

where $v, \Delta$—calibration constants $t_i^F$ i $t_i^T$—time of signal of the photomultiplier in the front and rear layer, respectively while as the final result the average weighted with appropriate measurement uncertainties is calculated.

Formulas I and II take into account information about the amplitudes of signals, while formula III uses arrival times of light signals to the photomultipliers. Formula III is based only on time information and is characteristic for this invention. Knowledge of the amplitudes distribution of signals in photomultipliers on the sides of plates allow to determine the depth of the interaction of the gamma quantum (DOI). For the calculation one use in the first approximation formula IV:

$$DOI = \frac{1}{4} \left[ \frac{\sum_i^{N_F} z_i A_F^i}{\sum_i^{N_F} A_F^i} + \frac{\sum_i^{N_T} z_i A_T^i}{\sum_i^{N_T} A_T^i} + \frac{\sum_i^{N_G} z_i A_G^i}{\sum_i^{N_G} A_G^i} + \frac{\sum_i^{N_D} z_i A_D^i}{\sum_i^{N_D} A_D^i} \right], \quad \text{(formula IV)}$$

where $z_1$—denotes the centre of ith photomultiplier along z axis (thickness of the plate).

FIG. 8 shows a gamma quantum and a scintillation plate.

Determination of the depth of interaction (DOI) of quantum is also an important feature of this invention. Knowing the coordinates r=(x, y, z) for the point of reaction for both gamma quanta r1 and r2 the LOR lines are determined.

Determination of the reaction point and knowledge of the amplitude and times of signals registered in photomultipliers allows calculation of the energy deposited by the gamma quantum in the scintillator material and time when the reaction occurred. This can be roughly calculated according to formulas V and VI, where the formula V:

$$t = \frac{1}{N} \sum_{I=1}^{N} t_i - \frac{\Delta r_i}{v_s}, \quad \text{(formula V)}$$

where

N—number of all the photomultipliers, which gave a signal by the reaction of a gamma quantum, $\Delta r_1$—the distance between the point of the reaction and the middle of the window of the ith photomultiptier $\Delta r_1 = |\vec{r} - \vec{r}_1|$ $v_s$—calibration constant corresponding to the speed of light of the signal in the scintillator, the formula VI:

$$E = \frac{\sum_{i=1}^{N} A_i |\Delta r|^2 \cdot e^{\frac{\Delta r}{\lambda}} / \sigma_i^2(A_i)}{\sum_{i=1}^{N} \frac{1}{\sigma_i^2(A_i)}}, \quad \text{(formula VI)}$$

where
λ—the calibration constant denoting attenuation of the signal,
σ—uncertainty of determination of the amplitude.
Knowing r1, r2, t1 and t2 we can calculate using TOP method. the point of annihilation along the LOR line from the formula VII:

$$\Delta LOR = \frac{t_2 - t_1}{2} c, \quad \text{(formula VII)}$$

where
C—speed of light.
FIG. 9 shows an annihilation point between scintillation plates.
Then the annihilation point $\vec{r}_a$ can be determined using the formula VIII:

$$\vec{r}_a = \frac{\vec{r_1} + \vec{r_2}}{2} + \frac{\vec{r_1} - \vec{r_2}}{|\vec{r_1} - \vec{r_2}|} \cdot \Delta LOR. \quad \text{(formula VIII)}$$

The described device provides a set of reconstructed LOR lines and the position of annihilation points along these lines. Based on these data one can obtain the tomographic image using image reconstruction techniques.

The invention claimed is:
1. A matrix device for determining a location and a time of a gamma quantum interaction and comprising a scintillation chamber, wherein said scintillation chamber comprises:
  (a) scintillation plates constructed out of a plastic scintillator doped with atoms with atomic number of at least 50, wherein surfaces of said scintillation plates are configured to reflect photons incident to said surfaces from inside of said scintillation chamber at an angle greater than a boundary angle,
  (b) photomultipliers forming detector walls and arranged as side layers (L, G, P, D) of said scintillation chamber and as a front layer (F) and a back layer (T) of said scintillation chamber for registering light pulses emerging from said scintillation chamber and for converting said light pulses into electronic signals,
  (c) a mounting plate attached from a housing for sheltering said matrix device wherein said photomultipliers are attached to said mounting plate an wherein said mounting plate is situated between said scintillation plates and said housing, and wherein said mounting plate has a net of culled holes, said holes having a size and a shape corresponding to a casing of each of said photomultipliers,
  (d) a frame attached to said housing, wherein said scintillation plates are embedded in said frame
  (e) an air layer between said photomultipliers and said scintillation planes and
  (f) and electronic system configured to:
    (i) select events for which said electronic signals were registered in at least three side layers (L, G, P, D) and in said front layer (F) and said back layer (T) of said scintillation chamber,
    (ii) include in further processing only those of said electronic signals which appeared within a fixed time interval,
    (iii) determine said location of said gamma quantum interaction in a plane of said scintillation plates as an average of calculations made with three independent methods:
      (1) based on amplitudes of said electronic signals from said front layer (P) and said back layer (T) of said scintillation chamber,
      (2) based on amplitudes of said electronic signals from said side layers (L, P, G, D) of said scintillation chamber, and
      (3) based on times of said electronic signals from said front layer (F) and said back layer (T) of said scintillation chamber
    (iv) determine a depth of gamma quantum interaction and lines of response for two coincident gamma quanta based on a distribution of electronic signal amplitudes in said photomultipliers of said side layers (L, G, P, D) of said scintillation chamber,
    (v) define an annihilation point along each of said lines of response based on times of said electronic signals from all said photomultipliers, and
    (vi) provides a tomographic picture based on a set of lines of response and said annihilation points along said lines of response.
2. The matrix device according to claim 1, further comprising voltage dividers for distributing voltage to photomultiplier dynodes.
3. The matrix device according to claim 1, wherein said scintillation plates are connected to each other by optical cement having a refractive index similar to a refractive index of a material from which said scintillation plates are made.
4. The matrix device according to claim 1, wherein said scintillation plates are separated from interior of said scintillation chamber with a light-proof foil.
5. The matrix device according to claim 1, wherein said scintillation chamber is lined with a plastic cover from a patient's side.
6. A method for determining a location and a time of a gamma quantum interaction in a matrix device comprising a scintillation chamber, wherein said scintillation chamber comprises:
  (a) scintillation plates made of plastic doped with atoms with atomic number of at least 50, wherein surfaces of said scintillation plates are configured to reflect photons incident to said surfaces from inside of said scintillation chamber at an angle greater than a boundary angle,
  (b) photomultipliers forming detector walls and arranged as side layers (L, P, G, D) of said scintillation chamber and as a front layer (F) and a back layer (T) of said scintillation chamber for registering light pulses emerging from said scintillation chamber and for converting said light pulses into electronic signals,
  (c) a mounting plate attached to a housing for sheltering said matrix device, wherein said photomultipliers are attached to said mounting plate, and wherein said mounting plate is situated between said scintillation plates and said housing, and wherein said mounting plate has a net of cut holes, said holes having a size and a shape corresponding to a casing of each of said photomultipliers,

(d) a frame attached to said housing, wherein said scintillation plates are embedded in said frame, and
(e) an air layer between said photomultipliers and said scintillation plates, the method comprising the steps of:
  (i) selecting events for which said electronic signals were registered in at least three side layers (L, G, P, D) and in said front layer (F) and said back layer (T) of said scintillation chamber,
  (ii) including in further processing only those of said electronic signals which appeared within a fixed time interval,
  (iii) determining said location of said gamma quantum interaction in a plane of said scintillation plates as an average of calculations made with three independent methods:
    (1) based on amplitudes of said electronic signals from said front layer (F) and said back layer (T) of said scintillation chamber,
    (2) based on amplitudes of said electronic signals from said side layers (L, G, P, D) of said scintillation chamber, and
    (3) based on times of said electronic signals from said front layer (F) and said back layer (T) of said scintillation chamber,
  (iv) determining a depth of said gamma quantum interaction and lines of response for two coincident gamma quanta based on a distribution of signal amplitudes in said photomultipliers of said side layers (L, G, P, D) of said scintillation chamber,
  (v) defining an annihilation point along each of said lines of response based on times of said electronic signals from all of said photomultipliers, and
  (vi) providing a tomographic picture based on a set of said lines of response and said annihilation points along said lines of response.

7. The method according to claim 6, further comprising the step of reconstructing a distribution of a density of a radioactive marker in a patient's body based on said location and said time of said gamma quantum interaction.

* * * * *

UNITED STATES PATENT AND TRADEMARK OFFICE
CERTIFICATE OF CORRECTION

PATENT NO. : 8,969,817 B2
APPLICATION NO. : 13/383581
DATED : March 3, 2015
INVENTOR(S) : Pawel Moskal Page 1 of 1

It is certified that error appears in the above-identified patent and that said Letters Patent is hereby corrected as shown below:

In the Claims

Column 9 line 55 should be corrected as follows:

Change:
-- from --
to
"to"

Column 10 line 16 should be corrected as follows:

Change:
-- (L,P,G,D) --
to
"(L,G,P,D)"

Column 10 line 55 should be corrected as follows:

Change:
-- (L,P,G,D) --
to
"(L,G,P,D)"

Signed and Sealed this
Twenty-third Day of June, 2015

Michelle K. Lee
*Director of the United States Patent and Trademark Office*